United States Patent [19]

Cherpeck

[11] Patent Number: 5,713,966
[45] Date of Patent: Feb. 3, 1998

[54] POLYALKYL HYDROXYAROMATIC ESTERS AND FUEL COMPOSITIONS CONTAINING THE SAME

[75] Inventor: Richard E. Cherpeck, Cotati, Calif.

[73] Assignee: Chevron Chemical Company, San Ramon, Calif.

[21] Appl. No.: 632,924

[22] Filed: Apr. 16, 1996

Related U.S. Application Data

[63] Continuation of Ser. No. 144,980, Oct. 28, 1993, abandoned.

[51] Int. Cl.$^6$ .................. C10L 1/18; C07C 69/88; C07C 69/76
[52] U.S. Cl. .................. 44/400; 560/67; 560/70; 560/71; 560/75
[58] Field of Search .................. 44/400; 560/67, 560/70, 71, 75

[56] References Cited

U.S. PATENT DOCUMENTS

| | | | |
|---|---|---|---|
| 2,479,326 | 8/1949 | De Verter | 44/400 |
| 3,285,855 | 11/1966 | Dexter et al. | 252/57 |
| 3,330,859 | 7/1967 | Dexter et al. | 560/75 |
| 3,849,085 | 11/1974 | Kreuz et al. | 44/78 |
| 4,049,713 | 9/1977 | Spivack | 560/75 |
| 4,113,442 | 9/1978 | Hoff et al. | 44/400 |
| 4,134,846 | 1/1979 | Machleder et al. | 252/51.5 A |
| 4,231,759 | 11/1980 | Udelhofen et al. | 44/75 |
| 4,320,021 | 3/1982 | Lange | 252/51.5 R |
| 4,347,148 | 8/1982 | Davis | 252/51.5 R |
| 4,713,475 | 12/1987 | Spivack et al. | 560/75 |
| 4,859,210 | 8/1989 | Franz et al. | 44/53 |
| 5,196,142 | 3/1993 | Mollet et al. | 252/311 |
| 5,196,565 | 3/1993 | Ross | 560/75 |
| 5,206,414 | 4/1993 | Evans et al. | 560/75 |
| 5,449,518 | 9/1995 | Junino et al. | 560/75 |
| 5,481,023 | 1/1996 | Kleiner et al. | 560/75 |

FOREIGN PATENT DOCUMENTS 3041444  2/1988  Japan.

*Primary Examiner*—Jerry D. Johnson
*Attorney, Agent, or Firm*—Claude J. Caroli

[57] ABSTRACT

Polyalkyl hydroxyaromatic esters having the formula:

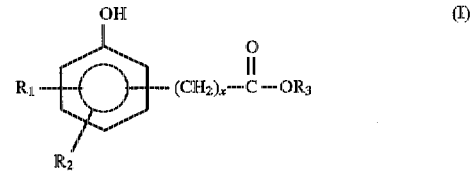

or a fuel-soluble salt thereof; where $R_1$ and $R_2$ are independently hydrogen, hydroxy, lower alkyl having 1 to 6 carbon atoms, or lower alkoxy having 1 to 6 carbon atoms; $R_3$ is a polyalkyl group having a weight average molecular weight in the range of about 450 to 5,000; and x is an integer from 0 to 10.

The polyalkyl hydroxyaromatic esters of formula I are useful as fuel additives for the prevention and control of engine deposits.

19 Claims, No Drawings

POLYALKYL HYDROXYAROMATIC ESTERS AND FUEL COMPOSITIONS CONTAINING THE SAME

This is a continuation of application Ser. No. 08/144,980, filed Oct. 28, 1993 now abandoned.

BACKGROUND OF THE INVENTION

1. Field of the Invention

This invention relates to novel hydroxyaromatic compounds. More particularly, this invention relates to novel polyalkyl hydroxyaromatic esters and their use in fuel compositions to prevent and control engine deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to 0.25 volume percent of a high molecular weight aliphatic hydrocarbon-substituted phenol in which the aliphatic hydrocarbon radical has an average molecular weight in the range of about 500 to 3,500. This patent teaches that gasoline compositions containing minor amounts of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

Similarly, U.S. Pat. No. 4,134,846, issued Jan. 16, 1979 to Machleder et al., discloses a fuel additive composition comprising a mixture of (1) the reaction product of an aliphatic hydrocarbon-substituted phenol, epichlorohydrin and a primary or secondary mono- or polyamine, and (2) a polyalkylene phenol. This patent teaches that such compositions show excellent carburetor, induction system and combustion chamber detergency and, in addition, provide effective rust inhibition when used in hydrocarbon fuels at low concentrations.

Amino phenols are also known to function as detergents/dispersants, antioxidants and anti-corrosion agents when used in fuel compositions. U.S. Pat. No. 4,320,021, issued Mar. 16, 1982 to R. M. Lange, for example, discloses amino phenols having at least one substantially saturated hydrocarbon-based substituent of at least 30 carbon atoms. The amino phenols of this patent are taught to impart useful and desirable properties to oil-based lubricants and normally liquid fuels.

Nitro phenols have also been employed as fuel additives. For example, U.S. Pat. No. 4,347,148, issued Aug. 31, 1982 to K. E. Davis, discloses nitro phenols containing at least one aliphatic substituent having at least about 40 carbon atoms. The nitro phenols of this patent are taught to be useful as detergents, dispersants, antioxidants and demulsifiers for lubricating oil and fuel compositions.

In addition, U.S. Pat. No. 4,231,759, issued Nov. 4, 1980 to Udelhofen et al., discloses a fuel additive composition comprising the Mannich condensation product of (1) a high molecular weight alkyl-substituted hydroxyaromatic compound wherein the alkyl group has a number average molecular weight of about 600 to about 3,000, (2) an amine and (3) an aldehyde. This patent teaches that such Mannich condensation products provide carburetor cleanliness when employed alone, and intake valve cleanliness when employed in combination with a hydrocarbon carrier fluid.

U.S. Pat. No. 4,859,210, issued Aug. 22, 1989 to Franz et al., discloses fuel compositions containing (1) one or more polybutyl or polyisobutyl alcohols wherein the polybutyl or polyisobutyl group has a number average molecular weight of 324 to 3,000, or (2) a poly(alkoxylate) of the polybutyl or polyisobutyl alcohol, or (3) a carboxylate ester of the polybutyl or polyisobutyl alcohol. This patent further teaches that when the fuel composition contains an ester of a polybutyl or polyisobutyl alcohol, the ester-forming acid group may be derived from saturated or unsaturated, aliphatic or aromatic, acyclic or cyclic mono- or polycarboxylic acids.

U.S. Pat. No. 3,285,855, issued Nov. 15, 1966 to Dexter et al., discloses alkyl esters of dialkyl hydroxybenzoic and hydroxyphenylalkanoic acids wherein the ester moiety contains from 6 to 30 carbon atoms. This patent teaches that such esters are useful for stabilizing polypropylene and other organic material normally subject to oxidative deterioration. Similar alkyl esters containing hindered dialkyl hydroxyphenyl groups are disclosed in U.S. Pat. No. 5,196,565, which issued Mar. 23, 1993 to Ross.

U.S. Pat. No. 5,196,142, issued Mar. 23, 1993 to Mollet et al., discloses alkyl esters of hydroxyphenyl carboxylic acids wherein the ester moiety may contain up to 23 carbon atoms. This patent teaches that such compounds are useful as antioxidants for stabilizing emulsion-polymerized polymers.

It has now been discovered that certain polyalkyl hydroxyaromatic esters provide excellent control of engine deposits, especially intake valve deposits, when employed as fuel additives in fuel compositions. Moreover, these polyalkyl hydroxyaromatic esters have been found to produce fewer combustion chamber deposits than known aliphatic hydrocarbon-substituted phenolic fuel additives.

SUMMARY OF THE INVENTION

The present invention provides novel polyalkyl hydroxyaromatic esters which are useful as fuel additives for the prevention and control of engine deposits, particularly intake valve deposits.

The polyalkyl hydroxyaromatic esters of the present invention have the formula:

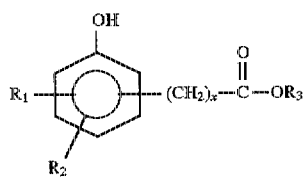

or a fuel-soluble salt thereof; wherein $R_1$ and $R_2$ are each independently hydrogen, hydroxy, lower alkyl having 1 to 6 carbon atoms, or lower alkoxy having 1 to 6 carbon atoms; $R_3$ is a polyalkyl group having a weight average molecular weight in the range of about 450 to 5,000; and x is an integer from 0 to 10.

The present invention further provides a fuel composition comprising a major amount of hydrocarbons boiling in the gasoline or diesel range and an effective deposit-controlling amount of a polyalkyl hydroxyaromatic ester of the present invention.

The present invention additionally provides a fuel concentrate comprising an inert stable oleophilic organic solvent boiling in the range of from about 150° F. to 400° F. and from about 10 to 70 weight percent of a polyalkyl hydroxyaromatic ester of the present invention.

Among other factors, the present invention is based on the surprising discovery that certain polyalkyl hydroxyaromatic esters, when employed as fuel additives in fuel compositions, provide excellent control of engine deposits, especially on intake valves, and produce fewer combustion chamber deposits than known aliphatic hydrocarbon-substituted phenolic fuel additives.

DETAILED DESCRIPTION OF THE INVENTION

The fuel additives provided by the present invention have the general formula:

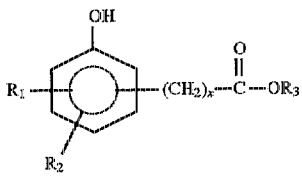

or a fuel-soluble salt thereof; wherein $R_1$, $R_2$, $R_3$, and x are as defined hereinabove.

Preferably, $R_1$ is hydrogen, hydroxy, or lower alkyl having 1 to 4 carbon atoms. More preferably, $R_1$ is hydrogen or hydroxy. Most preferably, $R_1$ is hydrogen.

$R_2$ is preferably hydrogen.

Preferably, $R_3$ is a polyalkyl group having a weight average molecular weight in the range of about 500 to 5,000, more preferably about 500 to 3,000, and most preferably about 600 to 2,000.

Preferably, x is an integer from 0 to 2. More preferably, x is 0.

A preferred group of polyalkyl hydroxyaromatic esters are those of formula I wherein $R_1$ is hydrogen, hydroxy, or lower alkyl having 1 to 4 carbon atoms; $R_2$ is hydrogen; and x is 0.

Another preferred group of polyalkyl hydroxyaromatic esters are those of formula I wherein $R_1$ is hydrogen, hydroxy, or lower alkyl having 1 to 4 carbon atoms; $R_2$ is hydrogen; and x is 1 or 2.

A more preferred group of polyalkyl hydroxyaromatic esters are those of formula I wherein $R_1$ is hydrogen or hydroxy; $R_2$ is hydrogen; and x is 0.

It is especially preferred that the aromatic hydroxyl group or groups present in the polyalkyl hydroxyaromatic esters of this invention be situated in a meta or para position relative to the polyalkyl ester moiety. When the aromatic moiety contains one hydroxyl group, it is particularly preferred that this hydroxyl group be in a para position relative to the polyalkyl ester moiety.

The polyalkyl hydroxyaromatic esters of the present invention will generally have a sufficient molecular weight so as to be non-volatile at normal engine intake valve operating temperatures (about 200°–250° C.). Typically, the molecular weight of the polyalkyl hydroxyaromatic esters of this invention will range from about 600 to about 6,000, preferably from 600 to 3,000, more preferably from 700 to 2,000.

Fuel-soluble salts of the polyalkyl hydroxyaromatic esters of the present invention are also contemplated to be useful for preventing or controlling deposits. Such salts include alkali metal, alkaline earth metal, ammonium, substituted ammonium and sulfonium salts. Preferred metal salts are the alkali metal salts, particularly the sodium and potassium salts, and the substituted ammonium salts, particularly tetraalkyl-substituted ammonium salts, such as the tetrabutylammonium salts.

Definitions

As used herein, the following terms have the following meanings unless expressly stated to the contrary.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "lower alkoxy" refers to the group —$OR_a$ wherein $R_a$ is lower alkyl. Typical lower alkoxy groups include methoxy, ethoxy, and the like.

The term "polyalkyl" refers to alkyl groups which are generally derived from polyolefins which are polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

General Synthetic Procedures

The polyalkyl hydroxyaromatic esters of this invention may be prepared by the following general methods and procedures. It should be appreciated that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

Moreover, those skilled in the art will recognize that it may be necessary to block or protect certain functional groups while conducting the following synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, *Protective Groups in Organic Synthesis*, Second Edition, Wiley, New York, 1991, and references cited therein.

In the present synthetic procedures, a hydroxyl group will preferably be protected, when necessary, as the benzyl or tert-butyldimethylsilyl ether. Introduction and removal of these protecting groups is well described in the art.

The polyalkyl hydroxyaromatic esters of the present invention having the formula:

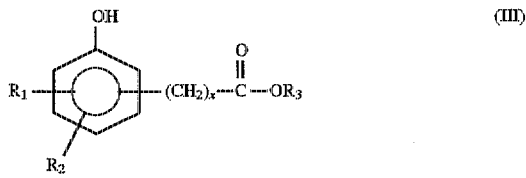

(III)

wherein $R_1$, $R_2$, $R_3$ and x are as defined above, may be prepared by esterifying a hydroxyaromatic carboxylic acid having the formula:

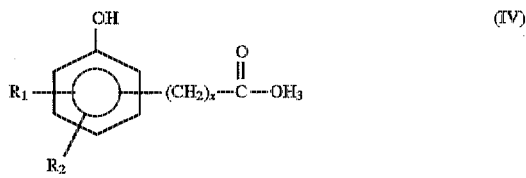

(IV)

wherein $R_1$, $R_2$, and x are as defined above, with a polyalkyl alcohol having the formula:

HO—$R_3$ (V)

wherein $R_3$ is as defined above, using conventional esterification reaction conditions.

The hydroxyaromatic carboxylic acids of formula IV are either known compounds or can be prepared from known compounds by conventional procedures. Suitable hydroxyaromatic carboxylic acids for use as starting materials in this invention are 2-hydroxybenzoic acid, 3-hydroxybenzoic acid, 4-hydroxybenzoic acid, 3,4-dihydroxybenzoic acid, 3,4,5-trihydroxybenzoic acid, 3-hydroxy-4-methoxybenzoic acid, 4-hydroxy-3-methoxybenzoic acid, 3-t-butyl-4-hydroxybenzoic acid, 3,5-di-t-butyl-4-hydroxybenzoic acid, 4-hydroxyphenylacetic acid, 3-(4-hydroxyphenyl)propionic acid and the like.

The polyalkyl alcohols of formula V may also be prepared by conventional procedures known in the art. Such procedures are taught, for example, in U.S. Pat. Nos. 5,055,607 to Buckley and 4,859,210 to Franz et al., the disclosures of which are incorporated herein by reference.

In general, the polyalkyl substituent on the polyalkyl alcohols of Formula V and the resulting polyalkyl hydroxyaromatic esters of the present invention will have a weight average molecular weight in the range of about 450 to 5,000, preferably about 500 to 5,000, more preferably about 500 to 3,000, and most preferably about 600 to 2,000.

The polyalkyl substituent on the polyalkyl alcohols employed in the invention may be generally derived from polyolefins which are polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

The preferred polyisobutenes used to prepare the presently employed polyalkyl alcohols are polyisobutenes which comprise at least about 20% of the more reactive methylvinylidene isomer, preferably at least 50% and more preferably at least 70%. Suitable polyisobutenes include those prepared using $BF_3$ catalysts. The preparation of such polyisobutenes in which the methylvinylidene isomer comprises a high percentage of the total composition is described in U.S. Pat. Nos. 4,152,499 and 4,605,808. Such polyisobutenes, known as "reactive" polyisobutenes, yield high molecular weight alcohols in which the hydroxyl group is at or near the end of the hydrocarbon chain.

Examples of suitable polyisobutenes having a high alkylvinylidene content include Ultravis 30, a polyisobutene having a molecular weight of about 1300 and a methylvinylidene content of about 74%, and Ultravis 10, a polyisobutene having a molecular weight of about 950 and a methylvinylidene content of about 76%, both available from British Petroleum.

The polyalkyl alcohols may be prepared from the corresponding olefins by conventional procedures. Such procedures include hydration of the double bond to give an alcohol. Suitable procedures for preparing such long-chain alcohols are described in I. T. Harrison and S. Harrison, *Compendium of Organic Synthetic Methods*, Wiley-Interscience, New York (1971), pp. 119–122, as well as in U.S. Pat. Nos. 5,055,607 and 4,859,210.

As indicated above, the polyalkyl hydroxyaromatic esters of formula III may be prepared by esterifying a hydroxyaromatic carboxylic acid of formula IV with a polyalkyl alcohol of formula V under conventional esterification reaction conditions.

Typically, this reaction will be conducted by contacting a polyalkyl alcohol of formula V with about 0.25 to about 1.5 molar equivalents of a hydroxyaromatic carboxylic acid of formula IV in the presence of an acidic catalyst at a temperature in the range of about 70° C. to about 160° C. for about 0.5 to about 48 hours. Suitable acid catalysts for this reaction include p-toluene sulfonic acid, methanesulfonic acid and the like. The reaction may be conducted in the presence or absence of an inert solvent, such as benzene, toluene and the like. The water generated by this reaction is preferably removed during the course of the reaction by, for example, azeotropic distillation with an inert solvent, such as toluene.

The polyalkyl hydroxyaromatic esters of formula III may also be synthesized by reacting a polyalkyl alcohol of formula V with an acyl halide having the formula:

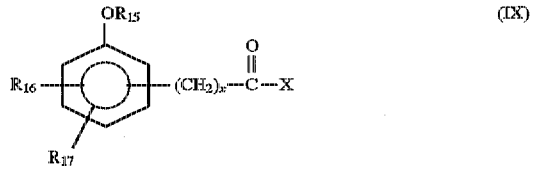

(IX)

wherein X is a halide, such as chloride or bromide, and $R_{15}$ is a suitable hydroxyl protecting group, such as benzyl, tert-butyldimethylsilyl, methoxymethyl, and the like; $R_{16}$ and $R_{17}$ are each independently hydrogen, lower alkyl, lower alkoxy, or the group —$OR_{18}$, wherein $R_{18}$ is a suitable hydroxyl protecting group.

Acyl halides of formula IX may be prepared from the hydroxyaromatic carboxylic acids of formula IV by first protecting the aromatic hydroxyl groups of formula IV to form a carboxylic acid having the formula:

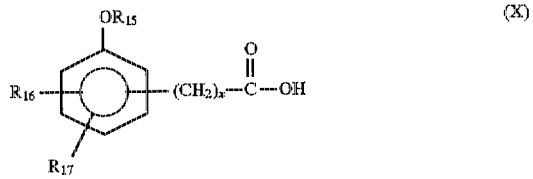

(X)

wherein $R_{15}$–$R_{17}$ and x are as defined above, and then converting the carboxylic acid moiety of formula X into an acyl halide using conventional procedures.

Protection of the aromatic hydroxyl groups of formula IV may be accomplished using well known procedures. The choice of a suitable protecting group for a particular hydroxyaromatic carboxylic acid will be apparent to those skilled in the art. Various protecting groups, and their introduction and removal, are described, for example, in T. W. Greene and P. G. M. Wuts, *Protective Groups in Organic Synthesis*, Second Edition, Wiley, New York, 1991, and references cited therein. Alternatively, the protected derivatives of formula X can be prepared from known starting materials other than the hydroxyaromatic compounds of formula IV by conventional procedures.

The carboxylic acid moiety of formula X may be converted into an acyl halide by contacting a compound of formula X with an inorganic acid halide, such as thionyl chloride, phosphorous trichloride, phosphorous tribromide, or phosphorous pentachloride; or alternatively, with oxalyl chloride. Generally, this reaction will be conducted using about 1 to 5 molar equivalents of the inorganic acid halide or oxalyl chloride, either neat or in an inert solvent, such as diethyl ether, at a temperature in the range of about 20° C. to about 80° C. for about 1 to about 48 hours. A catalyst, such as N,N-dimethylformamide, may also be used in this reaction.

In certain cases where the hydroxyaromatic carboxylic acids of formula IV having bulky alkyl groups adjacent to the hydroxyl group, such as 3,5-di-t-butyl-4-hydroxybenzoic acid, it will generally not be necessary to protect the hydroxyl group prior to formation of the acyl halide, since such hydroxyl groups are sufficiently sterically hindered so as to be substantially non-reactive with the acyl halide moiety.

Reaction of an acyl halide of formula IX with a polyalkyl alcohol of formula V provides an intermediate polyalkyl ester having the formula:

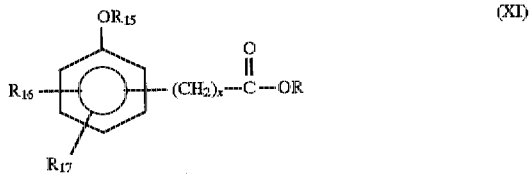

(XI)

wherein $R_3$, $R_{15}$–$R_{17}$, and x are as defined above.

Typically, this reaction is conducted by contacting an alcohol of formula V with about 0.9 to about 1.5 molar equivalents of an acyl halide of formula IX in an inert solvent, such as toluene, dichloromethane, diethyl ether, and the like, at a temperature in the range of about 25° C. to about 150° C. The reaction is generally complete in about 0.5 to about 48 hours. Preferably, the reaction is conducted in the presence of a sufficient amount of an amine capable of neutralizing the acid generated during the reaction, such as triethylamine, di(isopropyl)ethylamine, pyridine or 4-dimethylamino-pyridine.

Deprotection of the aromatic hydroxyl group(s) on the esters of formula XI then provides a polyalkyl hydroxyaromatic ester of formula III. Appropriate conditions for this deprotection step will depend upon the protecting group(s) utilized in the synthesis and will be readily apparent to those skilled in the art. For example, benzyl protecting groups may be removed by hydrogenolysis under 1 to about 4 atmospheres of hydrogen in the presence of a catalyst, such as palladium on carbon. Typically, this deprotection reaction is conducted in an inert solvent, preferably a mixture of ethyl acetate and acetic acid, at a temperature of from about 0° C. to about 40° C. for about 1 to about 24 hours.

Fuel Compositions

The polyalkyl hydroxyaromatic esters of the present invention are useful as additives in hydrocarbon fuels to prevent and control engine deposits, particularly intake valve deposits. The proper concentration of additive necessary to achieve the desired deposit control varies depending upon the type of fuel employed, the type of engine, and the presence of other fuel additives.

In general, the concentration of the polyalkyl hydroxyaromatic esters of this invention in hydrocarbon fuel will range from about 50 to about 2500 parts per million (ppm) by weight, preferably from 75 to 1,000 ppm. When other deposit control additives are present, a lesser amount of the present additive may be used.

The polyalkyl hydroxyaromatic esters of the present invention may be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to 8 carbon atoms, such as isopropanol, isobutylcarbinol, n-butanol and the like, in combination with hydrocarbon solvents are also suitable for use with the present additives. In the concentrate, the amount of the additive will generally range from about 10 to about 70 weight percent, preferably 10 to 50 weight percent, more preferably from 20 to 40 weight percent.

In gasoline fuels, other fuel additives may be employed with the additives of the present invention, including, for example, oxygenates, such as t-butyl methyl ether, anti-knock agents, such as methylcyclopentadienyl manganese tricarbonyl, and other dispersants/detergents, such as hydrocarbyl amines, hydrocarbyl poly(oxyalkylene) amines, or succinimides. Additionally, antioxidants, metal deactivators and demulsifiers may be present.

In diesel fuels, other well-known additives can be employed, such as pour point depressants, flow improvers, cetane improvers, and the like.

A fuel-soluble, nonvolatile carrier fluid or oil may also be used with the polyalkyl hydroxyaromatic esters of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, and synthetic polyoxyalkylene-derived oils, such as those described, for example, in U.S. Pat. No. 4,191,537 to Lewis, and polyesters, such as those described, for example, in U.S. Pat. Nos. 3,756,793 and 5,004,478 to Robinson and Vogel et al., respectively, and in European Patent Application Nos. 356,726 and 382,159, published Mar. 7, 1990 and Aug. 16, 1990, respectively.

These carrier fluids are believed to act as a carrier for the fuel additives of the present invention and to assist in removing and retarding deposits. The carrier fluid may also exhibit synergistic deposit control properties when used in combination with a hydroxyaromatic polyalkyl compound of this invention.

The carrier fluids are typically employed in amounts ranging from about 100 to about 5000 ppm by weight of the hydrocarbon fuel, preferably from 400 to 3000 ppm of the fuel. Preferably, the ratio of carrier fluid to deposit control additive will range from about 0.5:1 to about 10:1, more preferably from 1:1 to 4:1, most preferably about 2:1.

When employed in a fuel concentrate, carrier fluids will generally be present in amounts ranging from about 20 to about 60 weight percent, preferably from 30 to 50 weight percent.

EXAMPLES

The following examples are presented to illustrate specific embodiments of the present invention and synthetic preparations thereof; and should not be interpreted as limitations upon the scope of the invention.

Example 1

Preparation of Polyisobutyl 4-Hydroxybenzoate

To a flask equipped with a mechanical stirrer, thermometer, Dean Stark trap, reflux condenser and nitrogen inlet was added 525 grams of polyisobutanol (molecular weight average 984, prepared via hydroformylation of Amoco H-100 polyisobutene), 124.7 grams of 4-hydroxybenzoic acid, and 13.0 grams of p-toluene sulfonic acid. The mixture was stirred at 130° C. for sixteen hours, cooled to room temperature and diluted with 2 liters of diethyl ether. The organic phase was washed two times with saturated aqeous sodium bicarbonate, once with brine, dried over anhydrous magnesium sulfate, filtered and concentrated in vacuo to yield 514.3 grams of the desired product as a yellow oil. IR (neat) 1715, 1685 cm$^{-1}$; $^1$H NMR (CDCl$_3$) $\delta$7.95 (d, 2 H), 6.9 (d, 2 H), 5.8 (bs, 1 H), 4.3 (t, 2 H), 0.6–1.8 (m, 137 H).

Example 2

Preparation of Polyisobutyl 4-Hydroxyphenylacetate

To a flask equipped with a mechanical stirrer, thermometer, Dean Stark trap, reflux condenser and nitrogen inlet was added 35.0 grams of polyisobutanol (molecular weight average 984, prepared via hydroformylation of Amoco H-100 polyisobutene), 9.16 grams of 4-hydroxyphenylacetic acid, and 0.86 grams of p-toluene sulfonic acid. The mixture was stirred at 130° C. for sixteen hours, cooled to room temperature and diluted with 500 milliliters of diethyl ether. The organic phase was washed three times with methanol/water (4:1), once with brine, dried over anhydrous magnesium sulfate, filtered and concentrated in vacuo to yield 45.8 grams of a brown oil. The oil was chromatographed on silica gel eluting with hexane/ethyl acetate/ethanol (8:1.8:0.2) to yield 26.6 grams of the desired product as a yellow oil. IR (neat) 1714 cm$^{-1}$; $^1$H NMR (CDCl$_3$) $\delta$7.15 (d, 2 H), 6.75 (d, 2 H), 5.05 (bs, 1 H), 4.1 (t, 2 H), 3.5 (s, 2 H), 0.6–1.8 (m, 137 H).

Example 3

Preparation of Polyisobutyl Salicylate

To a flask equipped with a mechanical stirrer, thermometer, Dean Stark trap, reflux condenser and nitrogen inlet was added 35.0 grams of polyisobutanol (molecular weight average 984, prepared via hydroformylation of Amoco H-100 polyisobutene), 8.3 grams of salicylic acid, and 0.86 grams of p-toluene sulfonic acid. The mixture was stirred at 130° C. for sixteen hours, cooled to room temperature and diluted with 500 milliliters of diethyl ether. The organic phase was washed three times with methanol/water (4:1), once with brine, dried over anhydrous magnesium sulfate, filtered and concentrated in vacuo to yield 43.3 grams of a yellow oil. The oil was chromatographed on silica gel eluting with hexane/ethyl acetate/ethanol (8:1.8:0.2) to yield 26.4 grams of the desired product as a yellow oil. IR (neat) 1682 cm$^{-1}$; $^1$H NMR (CDCl$_3$) $\delta$10.8 (s, 1 H), 7.8 (d, 1 H), 7.4 (t, 1 H), 7.0 (d, 1 H), 6.8 (t, 1 H), 4.3 (t, 2 H), 0.6–1.8 (m, 137 H).

Example 4

Preparation of 4-Benzyloxy-2,6-dimethylbenzoyl Chloride

To a flask equipped with a magnetic stirrer and nitrogen inlet was added 11.35 grams of 4-benzyloxy-2,6-dimethylbenzoic acid (prepared as described by S. Thea, G. Cevasco, G. Guanti, No. Kashefi-Naini and A. Williams, *J. Org. Chem.*, 50, 1867 (1985)), 120 mL of anhydrous methylene chloride, followed by 9.7 mL of oxalyl chloride. The resulting mixture was stirred at room temperature for 16 hours and then the solvent was removed in vacuo to yield 11.4 grams of the desired acid chloride.

Example 5

Preparation of Polyisobutyl 4-Benzyloxy-2,6-dimethylbenzoate

4-Benzyloxy-2,6-dimethylbenzoyl chloride (5.3 grams) from Example 4 was combined with 13.5 grams of polyisobutanol (molecular weight average 984, prepared via hydroformylation of Amoco H-100 polyisobutene) and 200 mL of anhydrous toluene. Triethylamine (2.8 mL) and 4-dimethylaminopyridine (1.18 grams) were then added and the resulting mixture was heated to reflux under nitrogen for 16 hours. The reaction was cooled to room temperature and diluted with diethyl ether. The organic layer was washed twice with 1% aqeous hydrochloric acid, twice with saturated aqeous sodium bicarbonate solution, and once with brine. The organic layer was then dried over anhydrous magnesium sulfate, filtered and the solvents removed in vacuo to yield 17.8 grams of a brown oil. The oil was chromatographed on silica gel, eluting with hexane/ethyl acetate/ethanol (9:0.8:0.2), to yield 16.8 grams of the desired product as a brown oil.

Example 6

Preparation of Polyisobutyl 4-Hydroxy-2,6-dimethylbenzoate

A solution of 16.8 grams of the product from Example 5 in 100 mL of ethylacetate and 100 mL of acetic acid containing 3.0 grams of 10% palladium on charcoal was hydrogenolyzed at 35–40 psi for 16 hours on a Parr low-pressure hydrogenator. Catalyst filtration and removal of residual acetic acid with toluene in vacuo yielded 13.6 grams of the desired product as a yellow oil IR (neat) 1729, 1696 cm$^{-1}$; $^1$H NMR (CDCl$_3$) δ6.5 (s, 2 H), 5.0 (bs, 1 H), 4.3 (t, 2 H), 2.3 (s, 6 H), 0.6–1.8 (m, 137 H).

Example 7

Preparation of Polyisobutanol via Hydroboration

Polyisobutene (molecular weight average 700, available from Exxon as Parapol 700, 100 grams) was combined with anhydrous tetrahydrofuran (1.0 L) and cooled to 0° C. under nitrogen. Borane-tehydrahydrofurane complex (157 mL of a 1M solution of borane in tetrahydrofuran) was added dropwise and then the reaction was allowed to warm to room temperature and stirred for sixteen hours. 143 mL of 3N aqeous sodium hydroxide was added dropwise followed by 52.5 mL of 30% aqeous hydrogen peroxide. The mixture was stirred at room temperature for one hour and then diluted with 2.0 L of diethyl ether. The organic phase was washed three times with water, once with brine, dried over anhydrous magnesium sulfate, filtered and concentrated in vacuo to yield 96.4 grams of a yellow oil. The oil was chromatographed on silica gel eluting with hexane followed by hexane/ethyl acetate/ethanol (9:0.8:0.2) to yield 91 grams of the desired product as a light yellow oil.

Example 8

Preparation of 4-Benzyloxybenzoyl Chloride

To a flash equipped with a magnetic stirrer and drying tube was added 75.0 grams of 4-benzyloxybenzoic acid and 700 mL of anhydrous methylene chloride and then 72 mL of oxalyl chloride. The resulting mixture was stirred at room temperature for 16 hours and then the solvent was removed in vacuo to yield 79.6 grams of the desired acid chloride.

Example 9

Preparation of Polyisobutyl 4-Benzyloxybenzoate

4-Benzyloxybenzoyl chloride (6.9 grams) from Example 8 was combined with 20.0 grams of polyisobutanol from Example 7 and 200 mL of toluene. Triethylamine (4.1 mL) and 4-dimethylaminopyridine (1.70 grams) were then added and the resulting mixture was heated to reflux for 16 hours. The reaction was cooled to room temperature and diluted with diethyl ether. The organic layer was washed twice with 1% aqeous hydrochloric acid, twice with saturated aqeous sodium bicarbonate solution, and once with brine. The organic layer was then dried over anhydrous magnesium sulfate, filtered and the solvents removed in vacuo to yield 24.9 grams of a yellow oil. The oil was chromatographed on silica gel eluting with hexane/diethyl ether/ethanol (9:0.8:0.2), to yield 20.6 grams of the desired product as a light yellow oil.

Example 10

Preparation of Polyisobutyl 4-Hydroxybenzoate from Hydroborated Polyisobutene A solution of 20.6 grams of the product from Example 9 in 100 mL of ethylacetate and 100 mL of acetic acid containing 3.0 grams of 10% palladium on charcoal was hydrogenolyzed at 35–40 psi for 16 hours on a Parr low-pressure hydrogenator. Catalyst filtration and removal of residual acetic acid with toluene in vacuo yielded 19.2 grams of the desired product as a light yellow oil. IR (neat) 1716, 1682 cm$^{-1}$; $^1$H NMR (CDCl$_3$) δ8.0 (d, 2 H), 6.9 (d, 2 H), 5.1 (m, 1 H), 0.6–1.8 (m, 96 H).

Example 11

Single-Cylinder Engine Test

The test compounds were blended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 40° BTC; engine speed is 1800 rpm; the crankcase oil is a commercial 30W oil.

The amount of carbonaceous deposit in milligrams on the intake valves is reported for each of the test compounds in Table I and Table II.

TABLE I

| Sample[1] | Intake Valve Deposit Weight (in milligrams) | | |
|---|---|---|---|
| | Run 1 | Run 2 | Average |
| Base Fuel | 164.4 | 158.1 | 161.3 |
| Example 1 | 27.0 | 35.0 | 31.0 |
| Example 6 | 17.2 | 12.2 | 14.7 |
| Example 10 | 7.0 | 7.6 | 7.3 |

[1]At 200 parts per million actives (ppma).

TABLE II

| Sample[1] | Intake Valve Deposit Weight (in milligrams) | | |
|---|---|---|---|
| | Run 1 | Run 2 | Average |
| Base Fuel | 302.6 | 312.2 | 307.4 |
| Example 2 | 68.9 | 57.4 | 63.2 |
| Example 3 | 272.0 | 232.7 | 252.4 |

[1]At 200 parts per million actives (ppma).

The base fuel employed in the above single-cylinder engine tests was a regular octane unleaded gasoline containing no fuel detergent. The test compounds were admixed with the base fuel to give a concentration of 200 ppma (parts per million actives).

The data in Table I and Table II illustrates the significant reduction in intake valve deposits provided by the polyalkyl hydroxyaromatic esters of the present invention (Examples 1, 2, 3, 6 and 10) compared to the base fuel.

Example 12

Multicylinder Engine Test

The polyalkyl hydroxyaromatic esters of the present invention were tested in a laboratory multicylinder engine to evaluate their intake valve and combustion chamber deposit control performance. The test engine was a 4.3 liter, TBI (throttle body injected), V6 engine manufactured by General Motors Corporation.

The major engine dimensions are set forth in Table III:

Table III

| Engine Dimensions | |
| --- | --- |
| Bore | 10.16 cm |
| Stroke | 8.84 cm |
| Displacement Volume | 4.3 liter |
| Compression Ratio | 9.3:1 |

The test engine was operated for 40 hours (24 hours a day) on a prescribed load and speed schedule representative of typical driving conditions. The cycle for engine operation during the test is set forth in Table IV.

TABLE IV

| | Engine Driving Cycle | | | |
| --- | --- | --- | --- | --- |
| Step | Mode | Time in Mode [Sec][1] | Dynamometer Load [kg] | Engine Speed [RPM] |
| 1 | Idle | 60 | 0 | 800 |
| 2 | City Cruise | 150 | 10 | 1,500 |
| 3 | Acceleration | 40 | 25 | 2,800 |
| 4 | Heavy HWY Cruise | 210 | 15 | 2,200 |
| 5 | Light HWY Cruise | 60 | 10 | 2,200 |
| 6 | Idle | 60 | 0 | 800 |
| 7 | City Cruise | 180 | 10 | 1,500 |
| 8 | Idle | 60 | 0 | 800 |

[1]All steps, except step number 3, include a 15 second transition ramp. Step 3 includes a 20 second transition ramp.

All of the test runs were made with the same base gasoline, which was representative of commercial unleaded fuel. The results are set forth in Table V.

TABLE V

| Multicylinder Engine Test Results | | | |
| --- | --- | --- | --- |
| Sample[1] | | Intake Valve Deposits[2] | Combustion Chamber Deposits[2] |
| Base Fuel | Run 1 | 710 | 2339 |
| | Run 2 | 962 | 2059 |
| | Average | 836 | 2199 |
| Example 1 | Run 1 | 238 | 2317 |
| | Run 2 | 292 | 2418 |
| | Average | 265 | 2368 |

[1]At 200 parts per million actives (ppma).
[2]In milligrams (mg).

The base fuel employed in the above multicylinder engine tests contained no fuel detergent. The test compounds were admixed with the base fuel to give a concentration of 200 ppma (parts per million actives).

The data in Table V illustrates the significant reduction in intake valve deposits provided by the polyalkyl hydroxyaromatic esters of the present invention (Example 1) compared to the base fuel. Moreover, the data in Table V further demonstrates that the polyalkyl hydroxyaromatic esters of the present invention do not contribute significantly to combustion chamber deposits.

What is claimed is:

1. A compound of the formula:

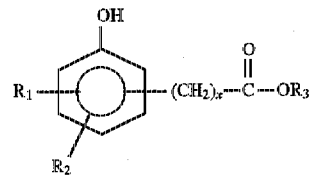

or a fuel-soluble salt thereof; wherein $R_1$ and $R_2$ are independently hydrogen, hydroxy, or lower alkoxy having 1 to 6 carbon atoms;

$R_3$ is a polyalkyl group having a weight average molecular weight in the range of 700 to 2,000; and x is 0.

2. The compound according to claim 1, wherein $R_1$ is hydrogen or hydroxy, and $R_2$ is hydrogen.

3. The compound according to claim 2, wherein $R_1$ and $R_2$ are hydrogen, and x is 0.

4. The compound according to claim 1, wherein $R_3$ is a polyalkyl group derived from polypropylene, polybutene, or polyalphaolefin oligomers of 1-octene or 1-decene.

5. The compound according to claim 4, wherein $R_3$ is derived from polyisobutene.

6. The compound according to claim 5, wherein the polyisobutene contains at least about 20% of a methylvinylidene isomer.

7. A fuel composition comprising a major amount of hydrocarbons boiling in the gasoline or diesel range and an effective detergent amount of a compound of the formula:

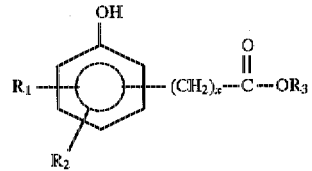

or a fuel-soluble salt thereof; wherein $R_1$ and $R_2$ are independently hydrogen, hydroxy, or lower alkoxy having 1 to 6 carbon atoms;

$R_3$ is a polyalkyl group having a weight average molecular weight in the range of 700 to 2,000; and x is 0.

8. The fuel composition according to claim 7, wherein $R_1$ is hydrogen or hydroxy, and $R_2$ is hydrogen.

9. The fuel composition according to claim 8, wherein $R_1$ and $R_2$ are hydrogen, and x is 0.

10. The fuel composition according to claim 7, wherein $R_3$ is a polyalkyl group derived from polypropylene, polybutene, or polyalphaolefin oligomers of 1-octene or 1-decene.

11. The fuel composition according to claim 10, wherein $R_3$ is derived from polyisobutene.

12. The fuel composition according to claim 11, wherein the polyisobutene contains at least about 20% of a methylvinylidene isomer.

13. The fuel composition according to claim 7, wherein said composition contains about 50 to about 2500 parts per million by weight of said compound.

14. A fuel concentrate comprising an inert stable oleophilic organic solvent boiling in the range of from about 150° F. to 400° F. and from about 10 to about 70 weight percent of a compound of the formula:

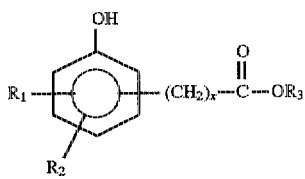

or a fuel-soluble salt thereof, wherein $R_1$ and $R_2$ are independently hydrogen, hydroxy, or lower alkoxy having 1 to 6 carbon atoms;

$R_3$ is a polyalkyl group having a weight average molecular weight in the range of 700 to 2,000; and x is 0.

15. The fuel concentrate according to claim 14, wherein $R_1$ is hydrogen or hydroxy, and $R_2$ is hydrogen.

16. The fuel concentrate according to claim 15, wherein $R_1$ and $R_2$ are hydrogen, and x is 0.

17. The fuel concentrate according to claim 14, wherein $R_3$ is a polyalkyl group derived from polypropylene, polybutene, or polyalphaolefin oligomers of 1-octene or 1-decene.

18. The fuel concentrate according to claim 17, wherein $R_3$ is derived from polyisobutene.

19. The fuel concentrate according to claim 18, wherein the polyisobutene contains at least about 20% of a methylvinylidene isomer.

* * * * *